United States Patent
Ratcliff et al.

[11] Patent Number: 5,968,090
[45] Date of Patent: Oct. 19, 1999

[54] ENDOVASCULAR GRAFT AND METHOD

[75] Inventors: Keith Ratcliff, Newtown; John Charles Robertson, Bloomfield, both of Conn.

[73] Assignee: United States Surgical Corp., Norwalk, Conn.

[21] Appl. No.: 08/925,281

[22] Filed: Sep. 8, 1997

[51] Int. Cl.$^6$ .................................................. A61F 2/06
[52] U.S. Cl. ........................................................ 623/1
[58] Field of Search ..................................... 623/1, 12

[56] References Cited

U.S. PATENT DOCUMENTS

| | | |
|---|---|---|
| 5,360,443 | 11/1994 | Barone et al. . |
| 5,522,880 | 6/1996 | Barone et al. . |
| 5,527,324 | 6/1996 | Krantz ........................................ 623/12 |
| 5,562,728 | 10/1996 | Lazarus et al. . |
| 5,571,171 | 11/1996 | Barone et al. . |
| 5,571,173 | 11/1996 | Parodi . |
| 5,578,071 | 11/1996 | Parodi . |
| 5,578,072 | 11/1996 | Barone et al. . |
| 5,591,197 | 1/1997 | Orth et al . |
| 5,591,226 | 1/1997 | Trerotola et al. . |
| 5,593,412 | 1/1997 | Martinez et al. . |
| 5,593,417 | 1/1997 | Rhodes . |
| 5,607,444 | 3/1997 | Lam . |
| 5,609,626 | 3/1997 | Quijano ........................................ 623/1 |
| 5,643,340 | 7/1997 | Nunokawa ................................... 623/1 |
| 5,769,870 | 6/1998 | Salehieh ...................................... 623/1 |
| 5,769,882 | 6/1998 | Fogarty ....................................... 623/1 |
| 5,782,904 | 7/1998 | White ......................................... 623/1 |

*Primary Examiner*—Michael J. Milano

[57] ABSTRACT

The endovascular graft disclosed includes a main tubular body having a first end portion and an exterior surface. The first end portion has a flanged end disposed on exterior surface and extending radially thereabout, for engaging blood vessel walls. The graft may be made from a surgically implantible material. The graft has a second end portion of the main body that can either be a continuation of the main body or split into two tubular legs. The two tubular legs, each define a bore. The bore of the main body is in communication with the bores of the legs.

A method of installing the endovascular graft includes installing the graft intraluminially to the operative site using a catheter having a balloon portion. The graft is positioned to extend through a damaged portion of a blood vessel. The balloon portion is positioned within a bore defined by the graft proximal to a first end portion, the first end portion having a flanged end. The balloon is expanded such that the flanged end expands into a blood vessel forming a raised portion on an exterior surface of the blood vessel. Finally, surgical clips are atraumatically applied to the raised portion compressing vessel tissue about the flanged end to capture the graft within the blood vessel.

18 Claims, 5 Drawing Sheets

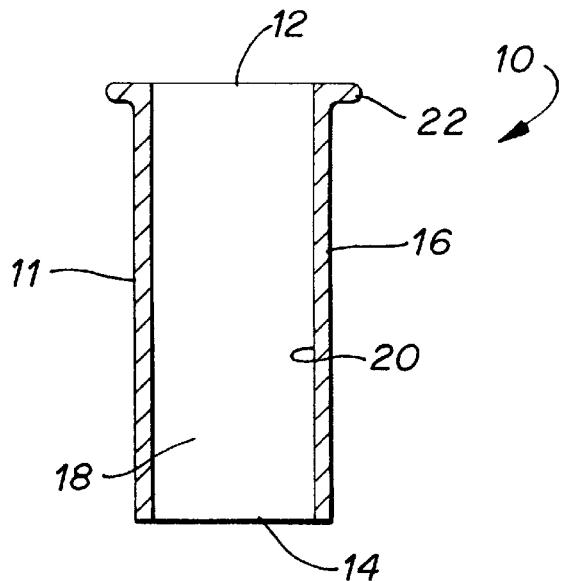
FIG_1
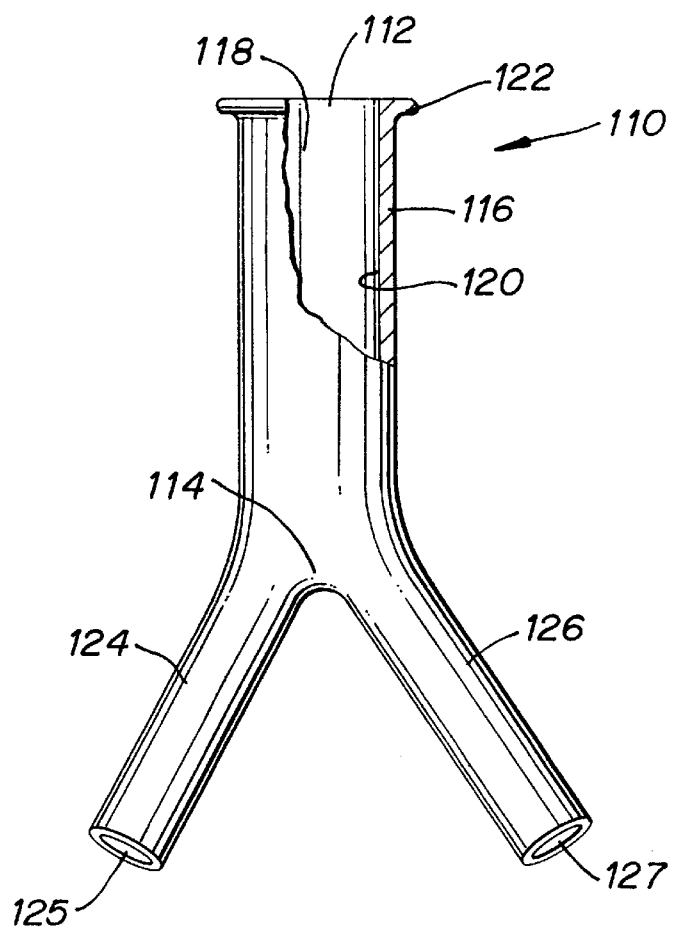
FIG_2

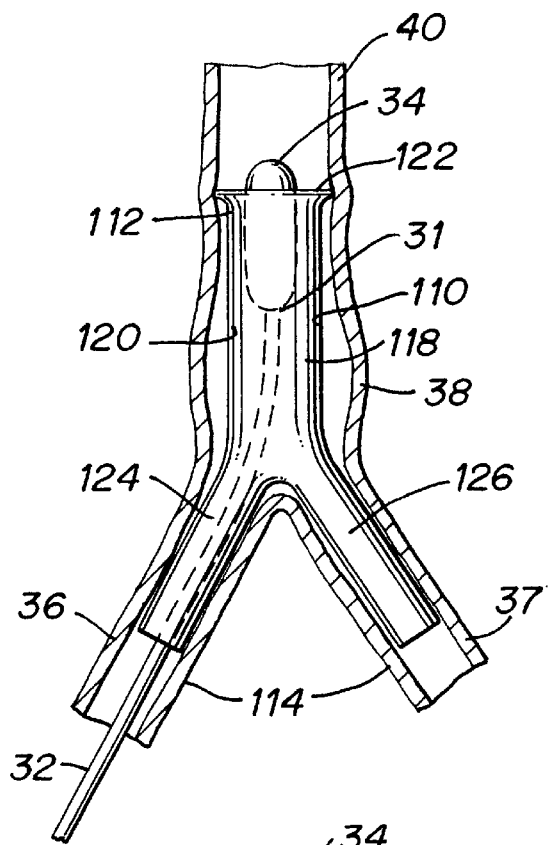
FIG_3
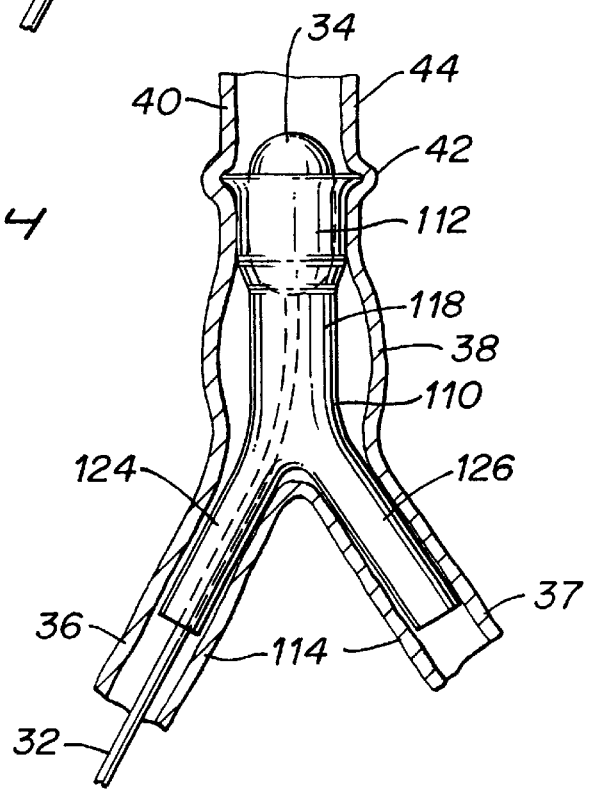
FIG_4

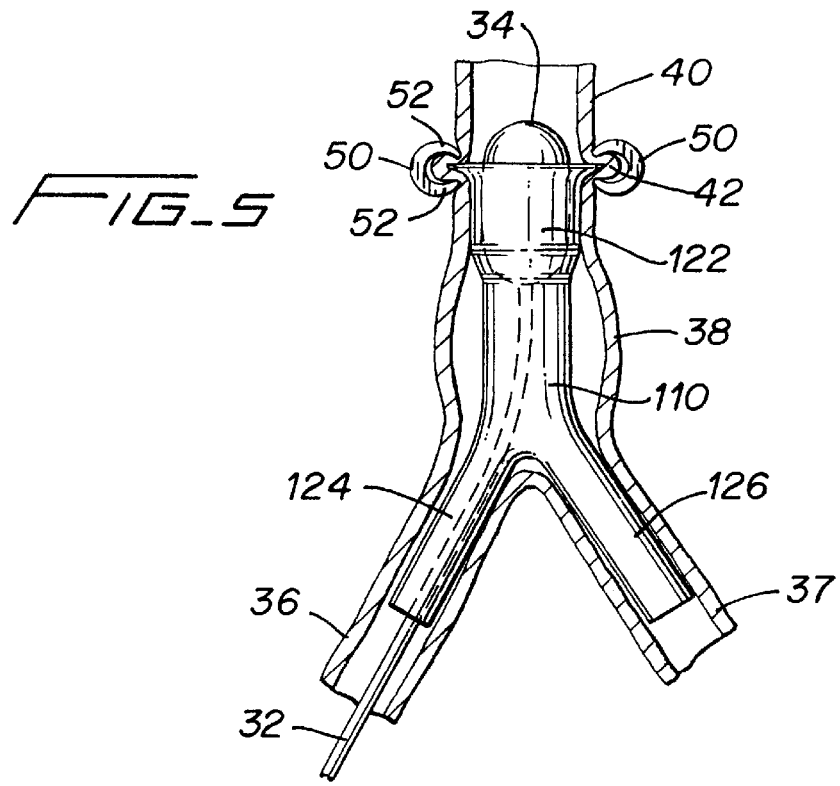
FIG_5
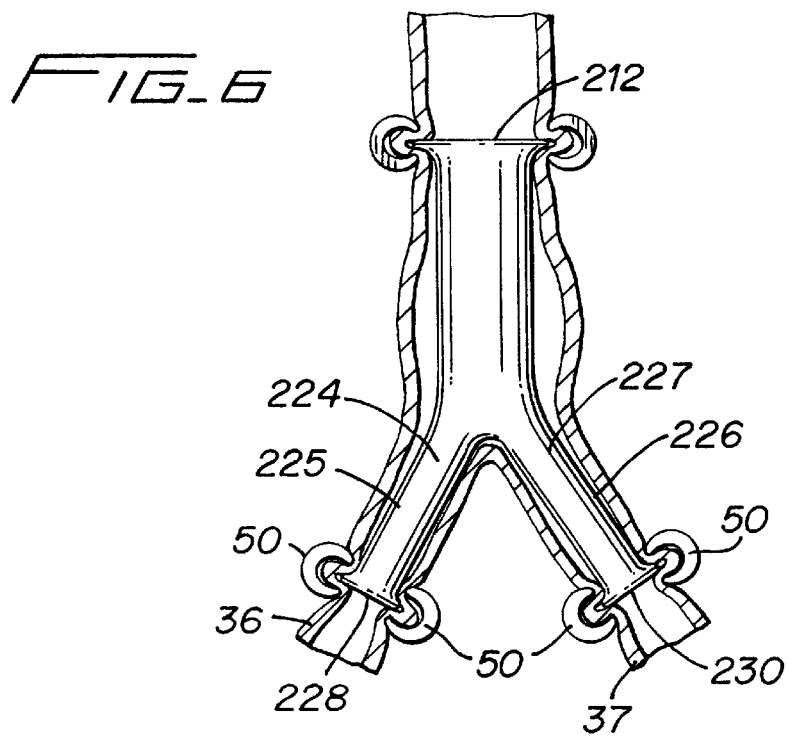
FIG_6

FIG. 7
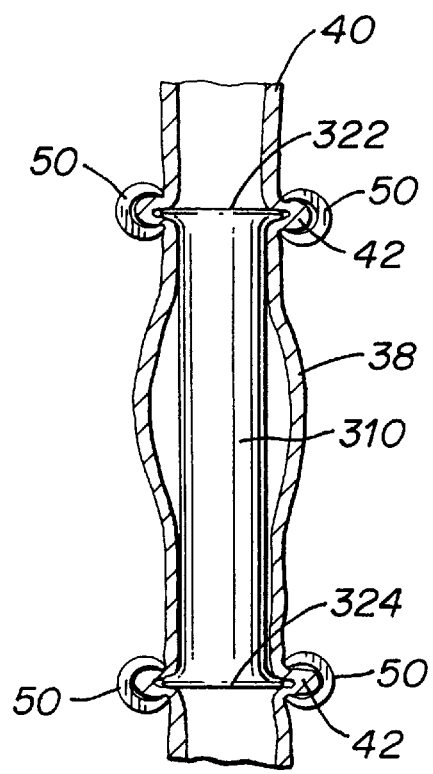
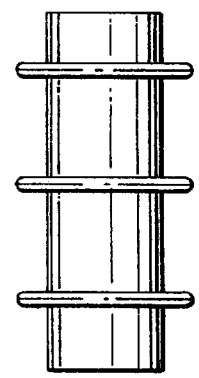
FIG. 8
FIG. 8A

ENDOVASCULAR GRAFT AND METHOD

BACKGROUND

1. Technical Field

This disclosure relates to a graft and, more particularly, to an endovascular graft having a flanged end to provide engagement to the walls of a blood vessel

2. Background of Related Art

Atherosclerosis is a major disease that effects the blood vessels. This disease may have its beginnings early in life and is first noted as a thickening of the arterial walls. This thickening is an accumulation of fat, fibrin, cellular debris and calcium. The resultant narrowing of the internal lumen of the vessel is called stenosis. Vessel stenosis impedes and reduces blood flow which can cause hypertension and dysfunction of the organ or area of the body that suffered the impaired blood flow.

As the buildup on the inner wall of the vessel thickens, the vessel wall loses the ability to expand and contract. Also, the vessel loses its viability and becomes weakened and susceptible to bulging, also known as aneurysm. In the presence of hypertension or elevated blood pressure, aneurysms will frequently dissect and ultimately rupture.

An abdominal aordic aneurysm is a sac caused by an abnormal dilation of the wall of the aorta as it passes through the abdomen, the portion of the body which lies between the thorax and the pelvis. The aorta arises from the left ventricle of the heart, passes upward, bends over and passes down through the thorax and through the abdomen where it divides into two iliac arteries. The aneurysm arises in the aorta near the region where the iliac arteries branch off. It is common for the aneurysm to expand from the aorta into the iliac arteries. When left untreated the aneurysm can rupture which can often lead to fatal hemorrhaging.

Transabdominal surgery to repair the aneurysm is a major undertaking with associated high risks. Performing the surgical procedure requires exposure of the aorta through an abdominal incision, which can extend from the rib cage to the pubis and requires moving the intestines to get to the back wall of the abdomen in order to clamp off the aorta. The aorta must be closed both above and below the aneurysm, so that the aneurysm can then be opened and the thrombus, or blood clot, and arteriosclerotic debris removed. A synthetic tube or graft is often sutured or stapled into place, thereby replacing the aneurysm. A graft with bifurcated ends is necessitated when the aneurysm has expanded into the iliac arteries.

With vascular suturing or stapling techniques for attaching the tube or graft, thrombosis or clotting may occur at the points of penetration which may cause occlusion of the vessels. In addition, suturing is a very tedious and time consuming process for surgeons to perform.

It would be advantageous to provide a method of securing a graft, atraumatically within a blood vessel that does not require suturing or stapling, yet still provides a reliable seal between the graft and the interior walls of the blood vessel. It would also be desirable to secure a graft to a section of a damaged blood vessel without making an incision in the blood vessel.

SUMMARY

The endovascular graft disclosed herein includes a tubular body having a first portion and an exterior surface. The first portion has a flange disposed on an exterior surface and extending radially thereabout for engaging the blood vessel wall to create a radially expanded portion of the vessel wall. The graft may be made from a surgically implantable material. The graft has a second portion remote from the first portion of the body that can either be a continuation of the body or split into two tubular legs. If split, the two tubular legs each define a bore and the bore of the body is in communication with the bores of the legs. The tubular legs may also have a flange for securing to the blood vessel.

A method of installing the vascular graft includes inserting the intraluminally to the operative site using a catheter having a balloon portion. The graft is positioned to extend through a damaged portion of a blood vessel. The balloon portion is positioned within a bore defined by the graft proximal to a first end portion which has a flange. The balloon is expanded such that the flange expands into a blood vessel forming a raised portion on an exterior surface of the blood vessel. Finally, surgical clips, preferably, non-penetrating, are atraumatically applied to the raised portion compressing vessel tissue about the flange to capture the graft within the blood vessel. If the graft is provided with more than one flange, the balloon is expanded at each of the flanges to form a raised surfaces on the blood vessel to enable application of surgical clips.

BRIEF DESCRIPTION OF THE DRAWINGS

The apparatus and method will be described in detail in the following description of preferred embodiments with reference to the following figures wherein:

FIG. 1 is a cross sectional view of a first embodiment of a graft having a flanged end;

FIG. 2 illustrates a plan view, with a portion cut away, of an alternate embodiment of the graft showing a bifurcated graft with a flanged end;

FIG. 3 is a cross sectional view of a blood vessel with the bifurcated graft of FIG. 2 positioned therein;

FIG. 4 is a cross-sectional view of the blood vessel with the bifurcated graft of FIG. 2 positioned herein showing a first end portion of the graft expanded;

FIG. 5 is a view similar to FIG. 4 showing non-penetrating surgical clips applied to the vessel to retain the first end portion of the graft;

FIG. 6 is a cross sectional view of a blood vessel with an alternate embodiment of the bifurcated graft positioned therein and retained by surgical clips at its three flanged ends;

FIG. 7 is a cross-sectional view of a blood vessel showing another alternate embodiment of the graft (non-bifurcated) positioned therein and secured to the vessel wall by surgical clips;

FIG. 8 is a plan view of yet another embodiment of the graft having a series of spaced apart flanges;

FIG. 8A illustrates formation of the flange; and

DETAILED DESCRIPTION OF PREFERRED EMBODIMENTS

Figure 9:
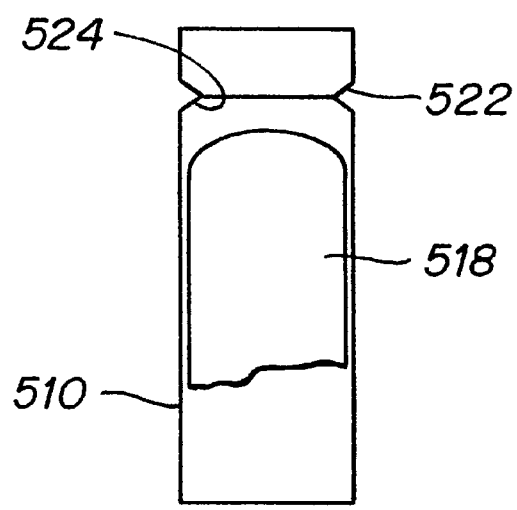
FIGS. 9 and 9A illustrate an alternate method of deploying the flanged region to form a raised portion in the vessel wall.

The present disclosure describes graft repair structure and methods used in repairing damaged blood vessel. The graft can be used for example within the aorta in the abdominal region to repair an aneurysm. Clearly, the graft can be used within other vessels.

Referring now in specific detail to the drawings in which like reference numerals identify similar or identical elements throughout the several views, and initially to FIG. 1, one embodiment of a graft constructed in accordance with a first embodiment of the present disclosure is shown generally as graft 10. Graft 10 includes a main tubular body 11 defining a longitudinal bore 18 therethrough. Graft 10 also includes a first end portion 12, a second end portion 14, an exterior surface 16 and an interior surface 20. Exterior surface 16 of first end portion 12 has a flanged end 22. Flanged end 22 creates a raised portion in the vessel wall as will be described below to allow application of non-penetrating clips. Second end portion 14 may optionally have a flanged end similar to flanged end 22 to enable securement to the vessel wall at second end portion 14. This is illustrated in FIG. 7. The flanged portion is deployed against the vessel wall by, for example, a balloon in the manner described below.

Referring now to FIG. 2, an alternate embodiment of the graft is illustrated in which second end portion 114 is bifurcated to allow graft 110 to be placed for example at the intersection between the aorta and iliac arteries. First tubular leg 124 and second tubular leg 126 each have longitinal bores 125 and 127, respectively, extending therethrough. Bores 125 and 127 communicate with bore 118. Flanged 122 is formed at first end portion 112. The interior and exterior surfaces are designated by reference numerals 20, 16 respectively. Legs 124 and 126 may also have flanged ends as in the embodiment of FIG. 6 described below.

Referring to FIG. 3, bifurcated graft 110 is shown disposed within a blood vessel 40. Blood vessel 40 may be for example in the aorta in the abdominal region with iliac arteries stemming therefrom. Graft 110 may be introduced into blood vessel 40 from a remote site such as through the femoral artery (not shown). Graft 10 is moved intraluminialy through the body to the operative repair site using a catheter 32. Catheter 32 has a balloon portion 34 which can be expanded enough to allow an interference fit between interior surface 120 of graft 110 and balloon portion 34. When the operative site is reached, graft 110 is placed such that at least a portion of first end portion 112 and second end portion 114, which has legs 124 and 126, extends beyond aneurysm 38 to engage healthy tissue. One method for deploying bifurcated graft 110 (not shown) across the aortic bifurcation and into the first and second iliac arteries 36 and 37 of a patient to repair an aneurysm includes folding leg 124 of the graft so it lies substantilly paralel to second leg 126 of graft 110 and introducing graft 110 through the femoral artery (not shown) until first end portion 112 of graft 110 is disposed proximal of the aortic aneurysm. The folded over leg 124 is then pulled down into second iliac artery 37, to position leg 124 of the graft in first iliac artery 36. Second leg 126 of graft 110 is positioned in second iliac artery 37.

Referring to FIG. 4, graft 110 is shown in position across the damaged arterial tissue and balloon portion 34 of catheter 32 is positioned within bore 118 proximal to first end portion 112. Catheter 32 introduces pressurized fluid into the balloon portion 34 forcing it to expand. The expansion of balloon portion 34 forces first end portion 112 to expand radially outward driving flanged end 122 into blood vessel 40. First end portion 112 is thereby moved to an expanded shape. Flanged end 122 causes a raised portion 42 (radially expanded portion) to form on the exterior portion 44 of blood vessel 40.

Referring to FIG. 5, balloon portion 34 remains expanded to aid in the application of surgical clips 50. Surgical clips 50 are introduced to clip raised portion 42 around flange 122. A plurality of surgical clips may be introduced one at a time or simultaneously. Surgical clips 50 are placed so that non-penetrating legs 52 are positioned about the raised portion 42 of blood vessel 40. Legs 52 are then deformed such that the vessel walls forming raised portion 42 are drawn together, and surgical clips 50 are applied without penetrating the vessel walls. Surgical clips 50 thus hold graft 110 in place while also providing a clamping force onto flanged end 122 to provide a seal against blood leakage around graft 110. These non-penetrating vascular surgical clips 50 are described in U.S. Pat. No. 5,591,178 the contents of which are incorporated herein by reference. The surgical clips 50 provide an atraumatic altertative to conventional fasteners such as sutures, staples, etc. since with suturing or stapling techniques, thrombosis or clotting may occur at the points of penetration through the walls of the vessel. After application of the clips 50, balloon portion 34 is deflated (not shown) and removed from the body.

An alternate embodiment of a bifurcated graft is shown in FIG. 6. Legs 224 and 226 have flanged ends 228 and 230, respectively. After the appropriate number of surgical clips 50 have been introduced on first end portion 212 in the same manner as described above, balloon portion 34 may be deflated and repositioned in leg 224 and in leg 226 within bores 225 or 227 (not shown). Balloon 234 can then be expanded proximate to flanged ends 228 and 230 to expand them into blood vessel 40 as previously performed on first end portion 212. After the balloon 234 has been used to separately inflate flanged ends 228, 230 it is deflated and removed from the body.

FIG. 7 illustrates an alternate embodiment in which graft 310 can be introduced into a blood vessel 40 in an area that is not bifurcated. Graft 310 has a flanged end 322 and a flanged end 324 and is designed for use in a straight section of blood vessel 40. FIG. 7 shows graft 310 installed within blood vessel 40 with both flanged ends 322 and 324 of graft 310 expanded to form a raised portion 42 in the vessel wall and secured thereto by surgical clips 50.

FIG. 8 illustrates another alternate embodiment in which graft 410 has a series of flanges along its length, illustratively spaced at about one centimeter intervals. This enables the user to cut the graft at a desired site to tailor the length of the graft to a particular use. The flanges can be formed, for example, by creasing and stiffening the graft at the site of the flange and pushing the portions of the graft an opposed sides of the flange together, as represented by the arrows of FIG. 8A.

Figure 9A:
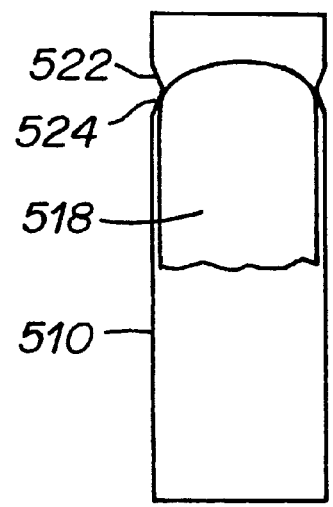

FIGS. 9 and 9A illustrates an alternate method of driving the flange of the graft radially outwardly against the blood vessel to form a raised portion for attachment of clips. In this method, once the graft is placed at the desired site, inner pusher 518 engages the camming surface 524 of the flange 522 to force it outwardly as shown in FIG. 9A. Complete advancement of the pusher 518 moves the flange radially outwardly (not shown) to force the vessel wall outwardly. Optionally, a sleeve (not shown) with a lip retains flange 522 of graft 510 in an inward position. The sleeve would be advanced to release the lip from engagement with flange 522 prior to advancing the pusher.

It will be understood that various modifications may be made to the embodiments disclosed herein. For example, although a catheter 32 with a balloon portion 34 is described for expanding flanged ends of graft 10, it is contemplated that other methods can be used for expanding the flanged ends into vessel wall 40. For example, shape memory alloy or spring release mechanisms can be utilized. Also, the flanges can be formed at other parts of the graft, e.g. spaced from the ends. Therefore, the above description should not be construed as limiting, but merely as exemplifications of preferred embodiments. Those skilled in the art will envision other modifications within the scope and spirit of the claims appended hereto.

What is claimed is:

1. A method of installing a vascular graft comprising the steps of:

inserting the graft intraluminially to an operative site;

positioning the graft across a damaged portion of a blood vessel;

expanding a flange of the graft into a vessel to form a raised portion on an exterior surface of the vessel; and applying surgical clips to the raised portion such that vessel tissue is compressed about the flange to capture the graft within the vessel.

2. The method as recited in claim 1, wherein the step of applying the surgical clips comprises deforming legs of the clip about the vessel tissue without penetrating the tissue.

3. The method as recited in claim 2 further comprising the steps of:

providing a flange on a second end portion of the graft, expanding the flange of the second end portion into a vessel forming a raised portion on an exterior surface of the vessel; and atraumatically applying surgical clips to the raised portion such that vessel tissue is sandwiched and compressed about the flange to capture the graft within the vessel.

4. The method as recited in claim 1 wherein the step of expanding the flange is performed using a balloon catheter.

5. The method as recited in claim 1, wherein the step of expanding the flange comprises advancing a pusher to contact and cam the flange outwardly.

6. The method as recited in claim 1 wherein the graft further comprises a second end portion, the second end portion having a first leg and a second leg and the step of inserting the graft comprises placing the legs in arteries of a bifurcated vessel portion.

7. The method as recited in claim 6 wherein the vessel is the aorta and the first and second arteries are iliac arteries.

8. The method as recited in claim 6 wherein the first leg has a flanged end and further comprising the steps of:

expanding the flanged end of the first leg into the vessel forming a raised portion on an exterior surface of the vessel; and atraumatically applying surgical clips to the raised portion such that vessel tissue is sandwiched and compressed about the flange to capture the graft within the vessel.

9. The method as recited in claim 6 wherein the step of expanding the flanged end of the first leg is performed using a balloon catheter.

10. The method as recited in claim 8 wherein the second leg has a flanged end and further comprising the steps of:

expanding the flanged end of the second leg into a vessel forming a raised portion on an exterior surface of the vessel; and atraumatically applying surgical clips to the raised portion such that vessel tissue is sandwiched and compressed about the flange to capture the graft within the vessel.

11. The method as recited in claim 10 wherein the step of expanding the flanged end of the second leg is performed using a balloon catheter.

12. A vascular graft system comprising:

a tubular body having a first end portion, a second end portion and an exterior surface, the first end portion having a flange extending radially thereabout for engaging an uninterrupted inner wall of a vessel to create a radially expanded portion of the vessel adjacent to the first end portion;

the second end portion having a flange extending radially thereabout for engaging an uninterrupted inner wall of a vessel to create a radially expanded portion of the vessel adjacent to the second end portion, a plurality of atraumatic surgical clips configured to engage an outer surface of the vessel adjacent the flanges of the first and second end portions.

13. A vascular graft system as recited in claim 12, wherein the second end portion includes two tubular legs, each of the legs defining a bore in fluid communication with a bore defined within the body, and each leg having a flange.

14. A vascular graft system comprising a tubular body having first end portion, a second end portion and an exterior surface, the first end portion having a flange extending radially thereabout for distending a vessel wall to create a radially expanded portion of the vessel wall; wherein the second end portion is remote from the first end portion, the second end portion having a flange and a plurality of surgical clips configured to radially engage the expanded portion of the vessel wall adjacent the first end portion.

15. A vascular graft system as recited in claim 14, further comprising a plurality of spaced apart flanges formed on the exterior surface of the graft.

16. A vascular graft system as recited in claim 14, wherein the plurality of surgical clips are atraumatic.

17. A vascular graft system comprising a tubular body having a first end portion, a second end portion and an exterior surface, the first end portion having a flange extending radially threabout for distending a vessel wall to create a radially expanded portion of the vessel wall wherein the second end portion is remote from the first end portion, the second end portion having two tubular legs, each of the legs defining a bore, and the main body defining a bore in communication with the bores of the legs; and a plurality of surgical clips configured to radially engage the expanded portion of the vessel wall adjacent the first end portion.

18. A vascular graft system as recited in claim 13 wherein at least one of the legs has a flanged portion.

* * * * *